(12) United States Patent
Keil

(10) Patent No.: US 10,824,695 B2
(45) Date of Patent: Nov. 3, 2020

(54) METHOD AND APPARATUS FOR DETERMINING A SIMILARITY PARAMETER FOR AN ORIGINAL PROTOCOL WITH A REFERENCE PROTOCOL FOR MEDICAL IMAGING

(71) Applicant: Siemens Healthcare GmbH, Erlangen (DE)

(72) Inventor: Miriam Keil, Erlangen-Dechsendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 567 days.

(21) Appl. No.: 15/697,774

(22) Filed: Sep. 7, 2017

(65) Prior Publication Data

US 2018/0068070 A1 Mar. 8, 2018

(30) Foreign Application Priority Data

Sep. 7, 2016 (DE) .......................... 10 2016 216 920

(51) Int. Cl.
| | | |
|---|---|---|
| *A61B 5/00* | (2006.01) | |
| *G06F 19/00* | (2018.01) | |
| *A61B 6/00* | (2006.01) | |
| *G16H 30/20* | (2018.01) | |
| *G16H 50/50* | (2018.01) | |
| *G16H 15/00* | (2018.01) | |
| *G16H 40/63* | (2018.01) | |
| *G06T 7/00* | (2017.01) | |
| *A61B 6/03* | (2006.01) | |

(52) U.S. Cl.
CPC .............. *G06F 19/321* (2013.01); *A61B 6/54* (2013.01); *G06T 7/0014* (2013.01); *G16H 15/00* (2018.01); *G16H 30/20* (2018.01); *G16H 40/63* (2018.01); *G16H 50/50* (2018.01); *A61B 6/032* (2013.01)

(58) Field of Classification Search
CPC ......... G06F 19/321; A61B 6/54; A61B 6/032; A61B 5/055; G16H 30/20; G16H 50/50; G16H 15/00; G16H 40/63; G06T 7/0014; G01R 33/36
See application file for complete search history.

(56) References Cited

U.S. PATENT DOCUMENTS

| | | | |
|---|---|---|---|
| 2012/0041909 A1 | 2/2012 | Glaser-Seidnitzer et al. | |
| 2012/0271840 A1* | 10/2012 | Vosniak ................ | G06F 19/321 707/758 |
| 2013/0129165 A1* | 5/2013 | Dekel .................... | G06F 19/321 382/128 |
| 2013/0129198 A1* | 5/2013 | Sherman ............... | G06F 19/321 382/159 |

\* cited by examiner

*Primary Examiner* — Joel Lamprecht
(74) *Attorney, Agent, or Firm* — Schiff Hardin LLP

(57) ABSTRACT

In a method and a medical imaging apparatus for determining a similarity parameter for an original protocol with a reference protocol, wherein the original protocol has control parameters for controlling a medical imaging apparatus and is compatible with an original configuration of the medical imaging apparatus, and the reference protocol has control parameters for controlling a medical imaging apparatus and is compatible with a new configuration, the similarity parameter is determined by a comparative analysis for the original protocol with the reference protocol.

22 Claims, 3 Drawing Sheets

METHOD AND APPARATUS FOR DETERMINING A SIMILARITY PARAMETER FOR AN ORIGINAL PROTOCOL WITH A REFERENCE PROTOCOL FOR MEDICAL IMAGING

BACKGROUND OF THE INVENTION

Field of the Invention

The invention concerns a method, a medical imaging apparatus, and a non-transitory, electronically readable data storage medium for determining a similarity parameter for an original protocol with a reference protocol, and a method, a medical imaging apparatus, a non-transitory electronically readable data storage medium for updating an original protocol.

Description of the Prior Art

A medical imaging apparatus is a system designed to perform medical imaging. Examples of medical imaging apparatuses include computed tomography scanners, magnetic resonance systems, positron emission tomography (PET) scanners, X-ray devices, and ultrasound devices. Medical imaging apparatuses generally have a number of components, which are typically controlled by software that includes algorithms. During control of medical imaging apparatuses, during medical imaging, image data are compiled depicting the anatomy or internal structure of an examination object in the form of sectional views or projections. An examination object can be, for example, a patient, a training volunteer or a phantom. The image data can be used as the basis for establishing clinical diagnoses and possibly for the diagnosis of diseases. The type of medical imaging apparatus to be used and typical control parameters for the control of the medical imaging apparatus are selected according to the clinical issue in question. Such control parameters are typically called a protocol. It may be necessary for the examination of a patient for the medical imaging apparatus to be controlled with a number of protocols that are different from one another.

A protocol is typically dependent upon the medical imaging apparatus and/or a component of the medical imaging apparatus and/or the installed software, and optionally takes into account individual requirements of a user of the medical imaging apparatus.

A protocol is typically determined once when there is a need to do so, and is then made available for selection for the subsequent examinations. Such a need exists, for example, on the installation of the medical imaging apparatus and/or in the case of user dissatisfaction with a protocol and/or in the case of change of the user who is the principal operator of the medical imaging apparatus and/or who evaluates the image data thereof. A protocol determined in this way, and that is available for selection during an examination with the medical imaging apparatus, can be called the original protocol. Following a change to a component of the medical imaging apparatus and/or on the installation of software, it may be no longer possible to implement the original protocol and/or it may be possible that another protocol is able to make better utilization of the changed component and/or the software, so that it may be necessary to update the original protocol.

SUMMARY OF THE INVENTION

An object of the invention is to provide a particularly simple and precise method for determining a similarity parameter for an original protocol with a reference protocol. A further object of the invention is to provide a particularly simple method for updating an original protocol.

The method according to the invention for determining a similarity parameter for an original protocol with a reference protocol, wherein the original protocol includes control parameters for controlling a medical imaging apparatus and is compatible with an original configuration of the medical imaging apparatus, and wherein the reference protocol includes control parameters for controlling the medical imaging apparatus and is compatible with a new configuration thereof, causes the similarity parameter to be determined by a comparative analysis for the original protocol with the reference protocol.

The method according to the invention is not carried out for a specific examination object. The method according to the invention is carried out without a patient being examined even without a patient being positioned such that it would be possible to perform an examination with the medical imaging apparatus. When the method according to the invention is carried out, the medical imaging apparatus is not controlled. When the method according to the invention is carried out, no image data from a patient are generated during a clinical examination.

To use a medical imaging apparatus for medical imaging, the medical imaging apparatus, and/or components thereof, are controlled, and different control parameters can be selected in dependence on the medical imaging apparatus, the examination object and/or the clinical issue in question. Control parameters can be physical variables such as a voltage to be applied to a component, such as a radio-frequency coil or an X-ray tube. If the medical imaging apparatus is a magnetic resonance apparatus, a control parameter can specify a duration between two radio-frequency pulses and/or magnetic field gradients to be played out. Control parameters can characterize the image data to be recorded by specifying a resolution, for example.

Control parameters are typically selected in dependence on the examination object and/or the clinical issue in question, in particular in dependence on the reason for the examination, by operation of the medical imaging apparatus. A set of control parameters that can be used as the basis for controlling the medical imaging apparatus so as to generate image data is called a protocol. The image data generated with the control parameters of a protocol preferably have a uniform contrast and preferably display a sub-area of the examination object. In the case of examinations with magnetic resonance systems, during an examination, a sub-area of the examination object is displayed in at least one further contrast. To this end, it is possible to use a further protocol that includes other control parameters. Therefore, for the examination of an examination object, the medical imaging apparatus can be controlled by multiple protocols.

During the control of the medical imaging apparatus, the control parameters are, for example, forwarded to a control computer of the medical imaging apparatus, wherein said control computer controls at least one component according to the control parameters. If a control parameter is not a physical variable, the control computer can translate the control parameters into at least one physical variable.

The medical imaging apparatus is typically characterized by its configuration. For example, a configuration can involve information about the presence and/or embodiment (model) of a special component of the medical imaging apparatus. A configuration typically involves information about software of the medical imaging apparatus. For example, it is possible for an option and/or a limitation for a control parameter, and hence for a protocol, to be extracted from the configuration. A protocol is compatible with a configuration when the medical imaging apparatus can be controlled with the control parameters of the protocol. The original configuration is one configuration. The original protocol is compatible with the original configuration. When a property that changes the configuration of the medical imaging apparatus is modified, the changed configuration is called a new configuration. The reference protocol is compatible with the new configuration.

The reference protocol is preferably stored in a memory so that the reference protocol can be provided for implementation of the method. The memory can be a component of the medical imaging apparatus. The reference protocol can be generated by a specialist with respect to a specific examination, for example. A specialist can be a person working in the field of the development of the medical imaging apparatus. A specialist can be a person who adapts, in particular optimizes, the use of the medical imaging apparatus, in particular as a medical practitioner and/or in conjunction with a medical practitioner.

The comparative analysis implemented in accordance with the invention for the original protocol with the reference protocol determines a similarity parameter. The similarity parameter typically characterizes a difference between the original protocol and the reference protocol. The similarity parameter is preferably a measure for the conformity of the original protocol with the reference protocol. The similarity parameter is preferably a quantitative value. For example, the similarity parameter can assume the value 1 for conformity of the reference protocol with the original protocol and the value 0 for a maximum difference between the two protocols. The maximum difference can be, for example, all control parameters taken into account during the comparative analysis are different from one another and/or that the difference of at least one control parameter taken into account during the comparative analysis between the two protocols exceeds a threshold value.

The comparative analysis preferably includes a weighting and/or prioritization of control parameters of the original protocol and/or the reference protocol. The comparative analysis preferably takes account of a weighting and/or prioritization of a property that can be generated with the original protocol and/or the reference protocol. Weighting and/or prioritization can be specified by a user.

The user of the medical imaging apparatus is typically satisfied with the control of the medical imaging apparatus according to the original protocol and/or accustomed to the quality and/or the contrast of the image data generated according to the original protocol and the medical imaging apparatus. In the case of a new configuration of the medical imaging apparatus, it is possible that the original protocol may no longer be compatible with the new configuration. The user is typically interested in identifying a new protocol that corresponds most closely to the original protocol and/or makes better utilization of the changed component affected by the new configuration and/or the software than the original protocol.

The advantage of the method according to the invention is that it performs a comparative analysis for the original protocol with the reference protocol. The reference protocol is preferably a protocol matched to the new configuration. The reference protocol is compatible with the new configuration. The reference protocol preferably makes better utilization of the changed component affected by the new configuration and/or the software than the original protocol. Accordingly, the user of the medical imaging apparatus can compare the original protocol, which has optionally been individualized by the user, with a protocol that can be called the standard. The similarity parameter characterizes, in particular quantifies, differences between the original protocol and the reference protocol, thus enabling an objective comparison. Since the determination of the similarity parameter is performed according to a typically prespecified comparative analysis, the method can be carried out simply and/or precisely.

In an embodiment of the method, the comparative analysis involves a conversion of the original protocol so that the converted original protocol is compatible with the new configuration of the medical imaging apparatus.

The conversion is preferably performed such that the difference between the original protocol and the converted original protocol is minimized. If a comparative analysis for the original protocol with the reference protocol were performed, the similarity parameter would indicate a maximum similarity between the original protocol and the converted original protocol. If the comparative analysis involves a conversion of the original protocol, it is possible in all temporally successive method steps, in particular during the comparative analysis, for the converted original protocol to be used instead of the original protocol. A user of the medical imaging apparatus preferably selects and/or indicates, whether the converted original protocol should be used instead of the original protocol.

An advantage of the conversion of the original protocol is that that compatibility-induced differences between the original protocol and the converted original protocol, which typically occur in the case of new software, can be eliminated before the comparative analysis. If the comparative analysis and/or the similarity parameter relates to a similarity and/or a difference between the converted original protocol and a reference protocol, a similarity and/or a difference are determined between two protocols that are compatible with the new configuration and hence can be implemented. The reference protocol is preferably optimized for the new configuration. This enables an improvement in the display of differences and/or similarities between the reference protocol and an original protocol.

In another embodiment of the method, during the comparative analysis, a control parameter is selected and a comparison is performed between the original protocol and the reference protocol with respect to the control parameter. A user can select at least one control parameter, which is of particular interest to the user. The comparative analysis checks whether the original protocol and/or the reference protocol comprise the control parameter and/or the value of the control parameter in the original protocol and/or in the reference protocol. The similarity parameter characterizes, preferably quantifies, a result of the comparative analysis. An advantage of this embodiment is that a special control parameter can be taken into account in the comparative analysis. The similarity parameter preferably indicates a similarity between a reference protocol and the original protocol with reference to the control parameter. Hence, a user is given the possibility of determining the similarity of the protocols with respect to a special control parameter.

In another embodiment of the method, a user of the medical imaging apparatus determines a comparative set with control parameters to be taken into account during the comparative analysis and the control parameters comprised by the comparative set are taken into account during the comparative analysis.

The comparative set typically includes a control parameter that is usually used in a protocol for controlling the medical imaging apparatus. The user can determine at least one control parameter for the comparative set. During the selection of at least two control parameters for the comparative set, the user can prioritize and/or weight the at least two control parameters. The user can specify how the control parameters comprised by the comparative set influence the similarity parameter. To this end, the user can indicate a function, for example. The comparative analysis is preferably performed based on the control parameters of the comparative set. If the medical imaging apparatus is a magnetic resonance apparatus, the comparative set can include at least one of the following control parameters: spatial extension of the examination region, resolution of the examination region in the image data, number of slices, orientation of slices, echo time, repetition time, bandwidth of a RF pulse, bandwidth of a readout gradient, inversion time, acceleration factor in parallel imaging, undersampling rate.

An advantage of this embodiment is that a user of the medical imaging apparatus can observe control parameters of individual importance to the user during the comparative analysis. When specifying the comparative set, the user can specify the type of embodiment of the comparative analysis and/or the similarity parameter. This provides the user with transparency with respect to the similarity parameter and/or the user can use the comparative analysis individually and/or flexibly.

The invention also encompasses a method with which, based on a determined similarity parameter and an updating strategy, the original protocol is retained or the original protocol is replaced by a reference protocol.

The updating strategy defines the further method sequence in dependence on the similarity parameter. For example, the updating strategy can be designed such that a specific threshold value is specified for a quantitative similarity parameter. In this example, if the threshold value is exceeded, the original protocol can be replaced by the reference protocol. Alternatively, i.e. if the threshold value is fallen below, in this example, the original protocol can be retained. If the original protocol is retained, the original protocol is preferably converted such that it is compatible with the new configuration. If a converted original protocol has already been generated during the comparative analysis, the converted original protocol can replace the original protocol if the threshold value is fallen below. The same can apply to a threshold value that is qualitatively different and/or different in another way.

An advantage of this embodiment is that the original protocol, which with the new configuration is not compatible, can be replaced by a protocol compatible with the new configuration.

The reference protocol preferably makes better utilization of a changed component affected by the new configuration and/or the software than the original protocol, and hence the quality of the image data generated with the reference protocol is improved compared to the original protocol. According to this embodiment, the replacing protocol is determined such that the replacing protocol has a similarity with the original protocol defined by the updating strategy. This ensures that the selected protocol has a defined similarity with the original protocol, for example with respect to the quality of the image data to be generated therewith and/or with respect to a determined control parameter. With this embodiment of the method, a user of the medical imaging apparatus can ensure that a protocol is changed only to a defined degree in the case of a new configuration. With this embodiment of the method, a user of the medical imaging apparatus can ensure that the changed component affected by the new configuration and/or the software is used in future examinations with the medical imaging apparatus. The method can be performed quickly. If a user is using more than one medical imaging apparatus, the method can be carried out on all devices used by the user. Hence, the user obtains protocols that are compatible with the new configuration, optimized with respect to the new configuration and preferably generate image data of the same quality with different medical imaging apparatuses.

In an embodiment of the method for updating an original protocol, a reference set includes at least two reference protocols, and a similarity parameter for the original protocol with each reference protocol of the reference set is determined, and the original protocol is updated based on all similarity parameters and an updating strategy.

The reference set preferably includes multiple reference protocols that are compatible with the new configuration of the medical imaging apparatus. The reference set is preferably stored in a memory so that the reference set can be provided for the embodiment of the method. The reference set can be generated by a specialist with respect to different examination regions and/or clinical issues. The reference set can be provided in a new configuration of the medical imaging apparatus, for example in a memory. The memory can be a component of the medical imaging apparatus. The reference set preferably includes reference protocols that are typically used for the same clinical issue and/or an examination of the same organ and/or of the same examination region of the examination object as the original protocol.

A similarity parameter with the original protocol is determined for each of at least two of the reference protocols of the reference set. The similarity parameters are determined for the reference protocols of the reference set that are typically used for the same clinical issue and/or an examination of the same organ and/or of the same examination region of the examination object as the original protocol. Then, there are at least two similarity parameters for two different reference protocols. According to one updating strategy, the original protocol is updated based on the similarity parameters.

The updated original protocol is compatible with the new configuration of the medical imaging apparatus. If the similarity parameter is, for example, a quantitative value, the updating strategy can be that the reference protocol in the reference set that achieves the highest similarity parameter during the comparative analysis replaces the original protocol. Similarly, the updating strategy can be that the reference protocol in the reference set that achieves the highest similarity parameter during the comparative analysis only replaces the original protocol when the highest similarity parameter exceeds a defined threshold value. Herein, the comparative analysis is preferably performed taking account of control parameters defined in a comparative set. The threshold value is preferably matched to a function, wherein said function defines how the similarity parameter is determined and/or how the comparative analysis is performed.

When this embodiment of the method has been carried out, the updated protocol can be further adapted to user requirements. The updated protocol can be used as the basis for further individualization, wherein at least one control parameter of the updated protocol can be changed.

An advantage of this embodiment is that the original protocol is compared with at least two reference protocols that are compatible with the new configuration and optimized with respect to the new configuration and in each case a difference and/or a similarity is characterized. Hence, a user of the medical imaging apparatus can have an overview of protocols optimized for the new configuration and retain the similarity thereof to the original protocol. Consequently, when the original protocol is updated, a larger selection of reference protocols able to replace the original protocol is available. Information on the similarity of these protocols with the reference protocols can simplify the selection of a protocol for a user. The selection of a reference protocol and/or of the original protocol can be performed automatically in accordance with criteria stored in the updating strategy. This can ensure a high quality and/or similarity of the updated original protocol. Individual user requirements and/or wishes can be taken into account by means of the updating strategy. The method can be carried out by a user of the medical imaging apparatus, such as, for example, a radiologist or a technical assistant. In particular, preferably the presence of a specialist is not necessary to carry out the method and/or to check that the method has been carried out correctly. This enables a new configuration to be carried out inexpensively and flexibly. This enables a specialist to concentrate on tasks that the user is unable to perform. Thus, the specialist is able to work more efficiently.

In another embodiment of the method, the updating strategy is embodied such that the reference protocol for which the similarity parameter characterizes the smallest difference between the original protocol and the reference protocol replaces the original protocol during the updating.

An advantage of this embodiment of the method is that the original protocol is replaced by a reference protocol compatible with the new configuration, wherein the reference protocol is most similar to the original protocol. The user of the medical imaging apparatus can specify control parameters and/or prioritizations to be taken into account for the comparative analysis. The control parameters and/or prioritizations to be taken into account for the comparative analysis can also be specified in advance by a specialist so that a user of the medical imaging apparatus does not have to perform any individualization of the comparative analysis. According to this embodiment of the method, the updating can be performed automatically and preferably does not require any user interaction. This can ensure high quality of the updated original protocol. User wishes and/or requirements can be taken into account in the comparative analysis when determining the similarity parameter so that the updated original protocol is the reference protocol most closely corresponding to these user wishes and/or requirements.

In another embodiment of the method, the updating strategy specifies at least two categories for the reference protocols of the reference set and the updating of the original protocol comprises the following steps:

categorization of each of the reference protocols of the reference set in accordance with the respective similarity parameter into one of at least two categories, provision of the reference protocols as a first one of the at least two categories, selection of one of the protocols provided, which replaces the original protocol, or retention of the original protocol.

The updating strategy is preferably matched to a comparative set taken into account during the comparative analysis. The first category can also be formulated such that it includes reference protocols with a similarity parameter, wherein the similarity parameter indicates a similarity. Reference protocols similar to the original protocol preferably satisfy the user wishes indicated in a comparative set and/or updating strategy and are preferably optimized with respect to the new configuration of the medical imaging apparatus.

The second category can also be formulated so as to include reference protocols with a similarity parameter, wherein the similarity parameter indicates no similarity. To this end, it is, for example, possible for there to be a limit value for the similarity parameter. Reference protocols with a similarity parameter higher than the limit value can be assigned to the first category. Reference protocols with a similarity parameter lower than the limit value can be assigned to the second category.

Herein, the embodiment for the determination of the similarity parameter typically influences the categorization of a reference protocol. This can be influenced by the selection of a comparative set. The comparative set can, for example, comprise a first control parameter with a first weighting and a second control parameter with a second weighting. The first weighting can indicate that a similarity parameter determined by a comparative analysis for the original protocol with the reference protocol is only intended to indicate a similarity when the first control parameter and/or value thereof coincide in the original protocol and in the reference protocol. According to this example, the reference protocol can only be assigned to the first category when the first control parameter and/or the value thereof coincide in the original protocol and in the reference protocol. The second weighting can indicate that a similarity parameter determined by means of a comparative analysis for the original protocol with the reference protocol is only intended to indicate a similarity when a difference between the first control parameter in the original protocol and in the reference protocol is lower than a threshold value. According to the example, only then can the similarity parameter be higher than the limit value specified according to the updating strategy.

With the provision of the reference protocols as a first one of the at least two categories, these are displayed for example to a user for selection, for example on a display unit. The user can select one of the reference protocols provided to replace the original protocol for example by means of an input unit or cause the original protocol, possibly converted, to be retained. If the original protocol is retained, the original protocol is preferably converted during the updating.

Provision can also mean that the reference protocols as a first one of the at least two categories provides an algorithm, wherein the algorithm selects one of the reference protocols provided to replace the original protocol or causes the original protocol to be retained. The algorithm can take account of further information and/or control parameters and/or user requirements.

An advantage of this embodiment is that, proceeding from a reference set, it is first possible to preselect the reference protocols comprised by the reference set. Herein, it is in particular possible to select reference protocols similar to the original protocol. Then, in a second step, the preselection can be used as the basis for selecting the reference protocol to replace the original protocol. Preselection makes the updating of the original protocol clear and enables it to be carried out simply and intuitively.

In another embodiment of the method, during the provision, a difference between at least one reference protocol comprised by the first category and the original protocol is displayed.

A difference between a reference protocol and the original protocol can be displayed by displaying a control parameter that has a value that differs between the reference protocol and the original protocol. The display can be on a screen. Preferably, a number of control parameters, which may also be identical in the reference protocol and the original protocol, are displayed next to one another and control parameters that differ from one another in the reference protocol and the original protocol are highlighted, for example marked, in the display.

An advantage of this embodiment is that a user of the medical imaging apparatus is able to identify differences and common features between the reference protocol and the original protocol. The user can identify the causes of a similarity parameter and/or value thereof for a reference protocol, and based on the findings, make a better selection of an updated original protocol.

In another embodiment of the method, the updating strategy provides that the medical imaging apparatus is controlled according to the original protocol and/or according to at least one reference protocol. If a medical imaging apparatus is controlled according to a protocol and an examination object is arranged in or on the medical imaging apparatus, image data can be generated from the examination object. Image data generated according to the original protocol can be used as a standard when updating the original protocol. The image data recorded by execution of the updated original protocol preferably differs as little as possible from the standard and/or is even better compared to the standard.

If the medical imaging apparatus according to the original protocol and/or according to at least one reference protocol is controlled, image data sets generated thereby can be compared with one another. The user of the medical imaging apparatus can use the imaged data generated with different protocols as the basis for selecting the protocol to be used instead of the original protocol in future examinations. This enables the influence of changed control parameters on image quality to be investigated. This enables the user to select the updated original protocol intuitively and simply, in particular when the user is not familiar with the significance of a control parameter.

In another embodiment of the method, the updating strategy is determined by a user of the medical imaging apparatus. If the updating strategy is determined by a user, the updated original protocol preferably conforms to user wishes and/or requirements. This can eliminate the need for a further change to and/or individualization of the updated original protocol, for example by user adaptation of a control parameter.

In another embodiment of the method, the method is carried out according to a new configuration of the medical imaging apparatus. With the new configuration, the configuration of the medical imaging apparatus is typically changed. Prior to the new configuration, the medical imaging apparatus typically has an original configuration. Following the new configuration, the medical imaging apparatus typically has a new configuration. In the case of a new configuration, an original protocol can lose its compatibility with the configuration of the medical imaging apparatus. In this situation, determination of a similarity parameter and/or updating of an original protocol is particularly advantageous. In addition, a user is automatically notified of the new configuration by an automatic startup of the method according to the invention. This actively notifies the user of possible new features in the new configuration as a result of which there is a high probability of the user testing and/or using a new feature. This can increase user satisfaction.

The invention also encompasses a medical imaging apparatus with a control computer having a determining processor. The determining processor is designed to carry out the method according to the invention for determining a similarity parameter for an original protocol with a reference protocol.

The invention also encompasses a medical imaging apparatus with a control computer having a determining processor. The determining processor is designed to carry out the method according to the invention for updating the original protocol using a similarity parameter determined for an original protocol with a reference protocol, and by, implementing an updating strategy.

To this end, the determining processor has an input, a core processor and an output. Via the input, the determining processor is provided with the original protocol and/or a reference protocol and/or a comparative set and/or a control parameter. Further functions, algorithms or parameters required in the method can be provided for the determining processor via the input. The similarity parameter and/or further results of embodiments of the method according to the invention can be provided via the output. The determining processor can be integrated in the medical imaging apparatus. The determining processor can be installed separately from the medical imaging apparatus. The determining processor can be connected to the medical imaging apparatus.

The medical imaging apparatus can include an updating processor. The updating processor that is designed to carry out the method according to the invention for updating an original protocol.

The updating processor has an input, a core processor and an output. Via the input, the updating processor is provided with the original protocol and/or a reference protocol and/or a reference set and/or a similarity parameter and/or an updating strategy. Further functions, algorithms or parameters required in the method can be provided to the determining processor via the input. An updated original protocol and/or further results of an embodiment of the method according to the invention can be provided via the output. The updating processor can be integrated in the medical imaging apparatus. The updating processor can also be installed separately from the medical imaging apparatus. The updating processor can be connected to the medical imaging apparatus.

Embodiments of the medical imaging apparatus according to the invention correspond to the embodiments of the method according to the invention. The medical imaging apparatus can further have control components necessary or advantageous for carrying out the method according to the invention. It is also possible for the medical imaging apparatus to be designed to send control signals and/or to receive and/or process control signals in order to carry out a method according to the invention. The determining processor and/or the updating processor is preferably part of the control computer of the medical imaging apparatus according to the invention. A memory of the determining processor can be used to store computer programs and further software by which the processor unit of the determining processor automatically controls and/or carries out a method sequence of a method according to the invention.

The present invention also encompasses a non-transitory, computer-readable data storage medium encoded with programming instructions that, when the storage medium is loaded into a control computer or computer system of a medical imaging apparatus, cause the computer or computer system to implement any or all of the embodiments described above of the method in accordance with the invention for determining a similarity parameter and/or the method in accordance with the invention for updating an original protocol.

Examples of electronically readable data media are a DVD, a magnetic tape or a USB stick on which electronically readable control information, in particular software, is stored.

The advantages of the medical imaging apparatus according to the invention and the electronically readable data medium according to the invention substantially correspond to the advantages of the method according to the invention for determining a similarity parameter for an original protocol with a reference protocol and/or the advantages of the method according to the invention for updating an original protocol, which are explained in detail above. Features, advantages or alternative embodiments mentioned herein are also applicable to the other aspects of the invention.

DESCRIPTION OF THE PREFERRED EMBODIMENTS

Figure 1:
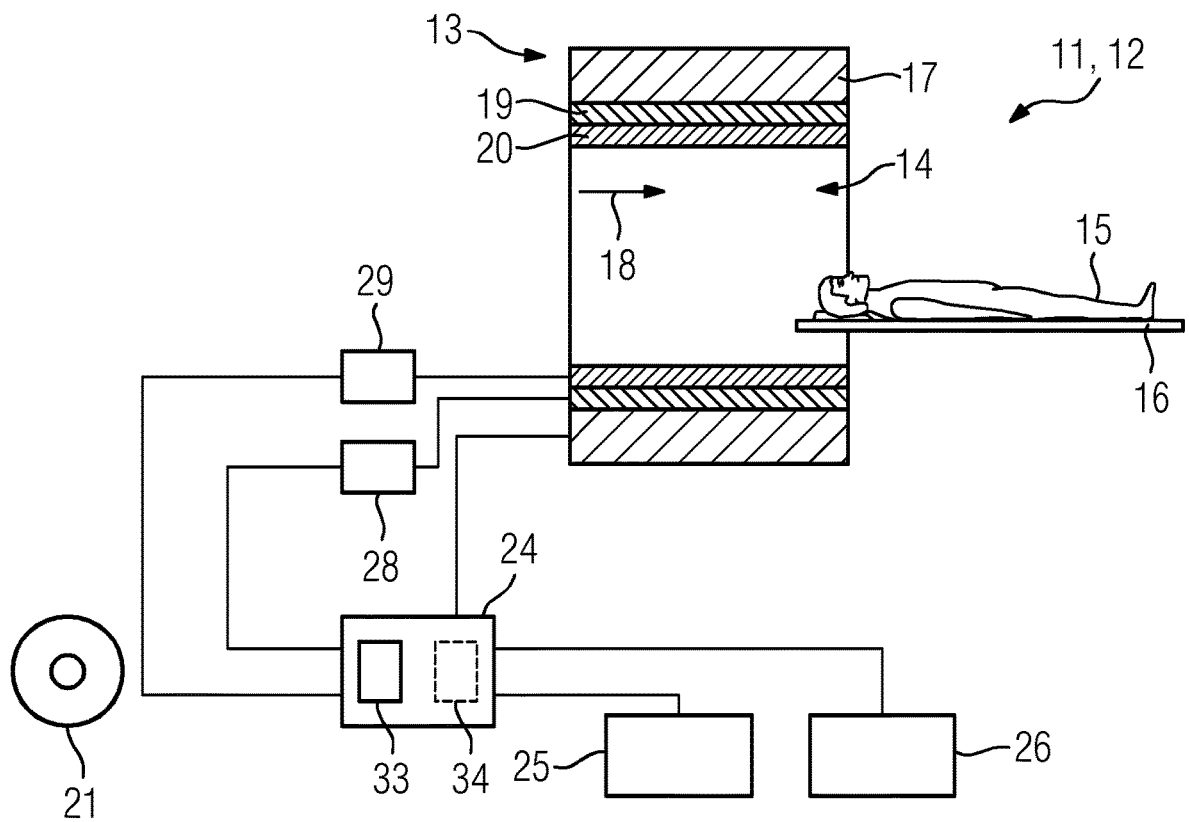
FIG. 1 is a schematic illustration of a medical imaging apparatus according to the invention.

FIG. 1 is a schematic illustration of a magnetic resonance apparatus 11 as an example of a medical imaging apparatus according to the invention for carrying out a method according to the invention. In principle, the embodiment of the medical imaging apparatus is not restricted to a magnetic resonance apparatus 11 but can be formed as other types of medical imaging apparatuses that appear reasonable to those skilled in the art, such as computed tomography scanners, PET devices, ultrasound devices, etc.

The magnetic resonance apparatus 11 has an MR data acquisition scanner 13 with a basic field magnet 17 that generates a strong and constant basic magnetic field 18. The scanner 13 also has a cylindrically shaped patient receiving area 14 for receiving a patient 15. The patient receiving area 14 is circumferentially surrounded in a cylindrical shape by the scanner 13. The patient 15 can be moved into the patient receiving area 14 by a patient-support apparatus 16. To this end, the patient-support 16 has a patient table that is movable within the scanner 13.

The scanner 13 further has a gradient coil arrangement 19 for spatially encoding MR signals during imaging. The gradient coil arrangement 19 is controlled by a gradient controller 28. The scanner 13 further has a radio-frequency (RF) antenna 20 that in the case shown, is designed as a body coil built into the scanner 13 and a radio-frequency antenna controller 29. The radio-frequency antenna 20 is controlled by the radio-frequency antenna controller 29 so as to emit radio-frequency pulses into an examination chamber substantially formed by the patient receiving area 14. The radio-frequency pulses cause certain nuclear spins in the patient 15 to deviate from the basic magnetic field 18 by an amount known as a flip angle. As these excited nuclear spins relax and return to the steady state, they emit the aforementioned magnetic resonance signals, which are received by the same antenna from which the excitation pulses were radiated, or by a different antenna.

To control the basic field magnet 17, the gradient controller 28 and the radio-frequency antenna controller 29, the magnetic resonance apparatus 11 has a control computer 24. The control computer 24 controls the magnetic resonance apparatus 11 centrally, such as for the performance of MR control sequences. The control computer 24 also has a reconstruction unit for the reconstruction of medical image data from the raw MR data acquired during the magnetic resonance examination. The magnetic resonance apparatus 11 has a display unit 25. Control information such as control parameters, and reconstructed image data can be displayed on the display unit 25, for example on at least one monitor, for a user. The magnetic resonance apparatus 11 also has an input unit 26, via which information and/or control parameters can be entered by a user during a scanning process. The control computer 24 can include the gradient controller 28 and/or the radio-frequency antenna controller 29 and/or the display unit 25 and/or the input unit 26.

The control computer 24 further has a determining processor 33. The determining processor 33 is also configured to carry out a method for determining a similarity parameter for an original protocol with a reference protocol. To this end, the determining processor 33 has computer programs and/or software, which can be loaded the directly into a memory of the determining processor 33 (not shown in further detail), with program means for carrying out a method for determining a similarity parameter for an original protocol with a reference protocol when the computer programs and/or software are executed in the determining processor 33. To this end, the determining processor 33 has a core processor (not shown) configured to execute the program code. The computer code can be stored on an electronically readable data storage medium 21 embodied separately from the control computer 24 and/or determining processor 33, with the determining processor being able to access the on the electronically readable data storage medium 21.

The control computer 24 can optionally have an updating processor 34. The updating processor 34 is configured to update an original protocol. To this end, the updating processor 34 has computer programs and/or software, which can be loaded directly into memory of the updating processor 34 (not shown in further detail), with program code for carrying out a method for updating an original protocol when the computer programs and/or software are executed in the updating processor 34. To this end, the updating processor 34 has a core processor (not shown), configured to execute the computer code and/or software. The computer code can be stored on an electronically readable data storage medium 21 embodied separately from the control computer 24 and/or updating processor 34, with the updating processor 34 being able to access the code on the electronically readable data storage medium 21.

The magnetic resonance apparatus 11 can also have further components that are usual for a magnetic resonance apparatus. The general mode of operation of a magnetic resonance apparatus is known to those skilled in the art so that a more detailed description is not necessary herein. The magnetic resonance apparatus 11 is configured together with the determining processor 33, and possibly the updating processor 34, to carry out a method according to the invention.

A method for determining a similarity parameter for an original protocol with a reference protocol can be provided in the form of program code that causes the determining processor 33 to implement the method when executed in the determining processor 33. An electronically readable data medium 21 has the electronically readable program code stored thereon.

Figure 2:
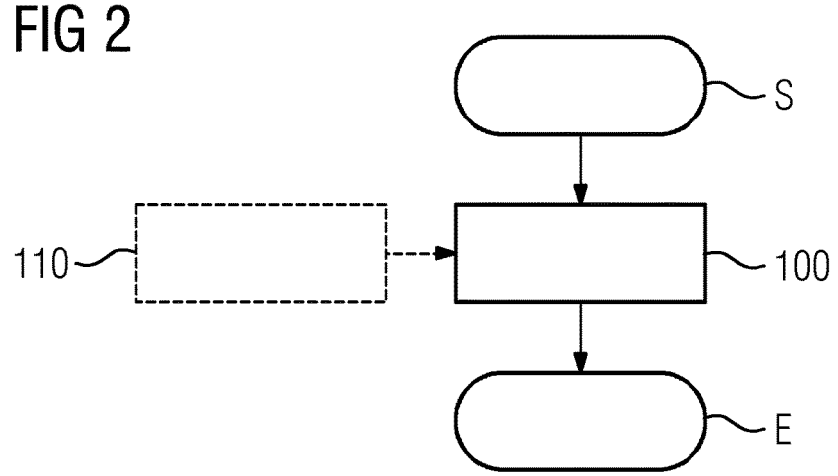
FIG. 2 is a flowchart of a first embodiment of a first method according to the invention.

FIG. 2 is a flowchart of a first embodiment of a first method according to the invention for determining a similarity parameter for an original protocol with a reference protocol. At the start S of the method, typically the original protocol and the reference protocol are provided. The original protocol has control parameters for controlling a medical imaging apparatus and is compatible with an original configuration of the medical imaging apparatus. The reference protocol has control parameters for controlling a medical imaging apparatus and is compatible with a new configuration of the medical imaging apparatus. In method step 100, a comparative analysis for the original protocol with the reference protocol is performed, wherein a similarity parameter is determined. To this end, it optionally possible in method step 110 for a user of the medical imaging apparatus to determine a comparative set with control parameters to be taken into account during the comparative analysis. The control parameters of the comparative set can be taken into account during the comparative analysis in method step 100. Method step 110 is preferably performed before method step 100. Method step 110 can also be performed before the start of the method S. Method step 100 is preferably carried out by the determining processor 33 of the medical imaging apparatus. According to the first embodiment, method step 100 preferably does not require any interaction on the part of a user of the medical imaging apparatus.

The similarity parameter determined in method step 100 typically characterizes a difference between the original protocol and the reference protocol. The method described in FIG. 2 is preferably carried out after a new configuration of the medical imaging apparatus 12. Method step 100 is followed by the end E of the method according to the invention.

Figure 3:
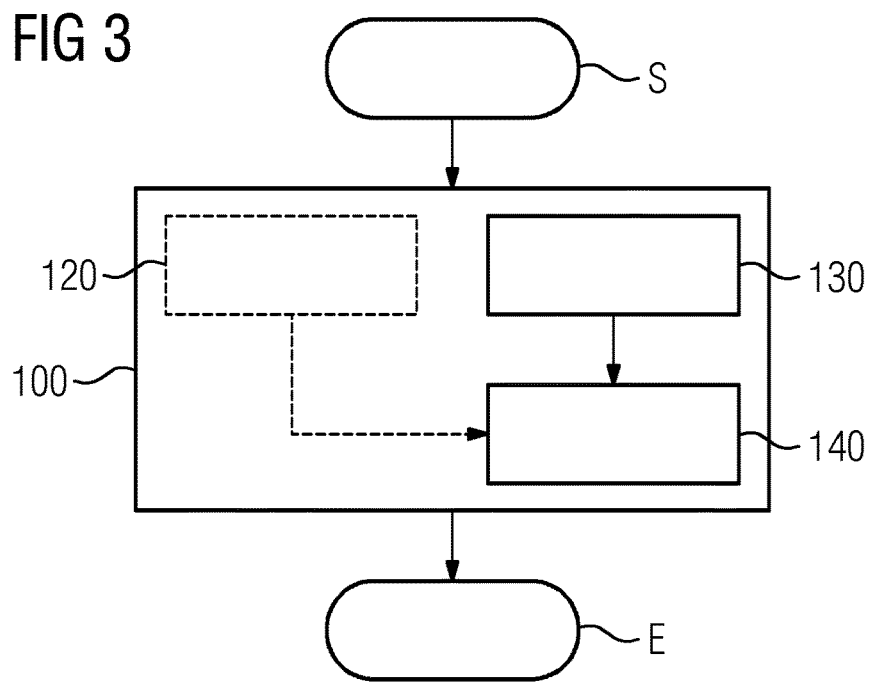
FIG. 3 is a flowchart of a second embodiment of the first method according to the invention.

FIG. 3 is a flowchart of a second embodiment of a first method according to the invention. It differs from the embodiment shown in FIG. 2 in detailed information on method step 100. In method step 100, a comparative analysis for the original protocol with the reference protocol is performed, wherein a similarity parameter is determined. Method step 100 can comprise further method steps. A selection of a control parameter can be performed in the method step 130, which is optionally a part of method step 100. The selection is preferably made by a user of the medical imaging apparatus. A comparison between the original protocol and the reference protocol with respect to the control parameter selected in method step 130 can be performed in the method step 140, which is optionally comprised by method step 100. Method step 100 can additionally comprise a conversion 120 of the original protocol so that the converted original protocol is compatible with the new configuration of the medical imaging apparatus. The conversion 120 is preferably performed before the comparison in method step 140 so that the comparison between the converted original protocol and the reference protocol is performed. However, the conversion 120 is independent of the performance of the method steps 130 and 140. Method step 100 is preferably performed by means of the determining processor 33 of the medical imaging apparatus. The selection of a control parameter and/or interaction in method step 130 can be performed by a user via the input unit 26 and/or display unit 25 of the magnetic resonance apparatus 12.

Figure 4:
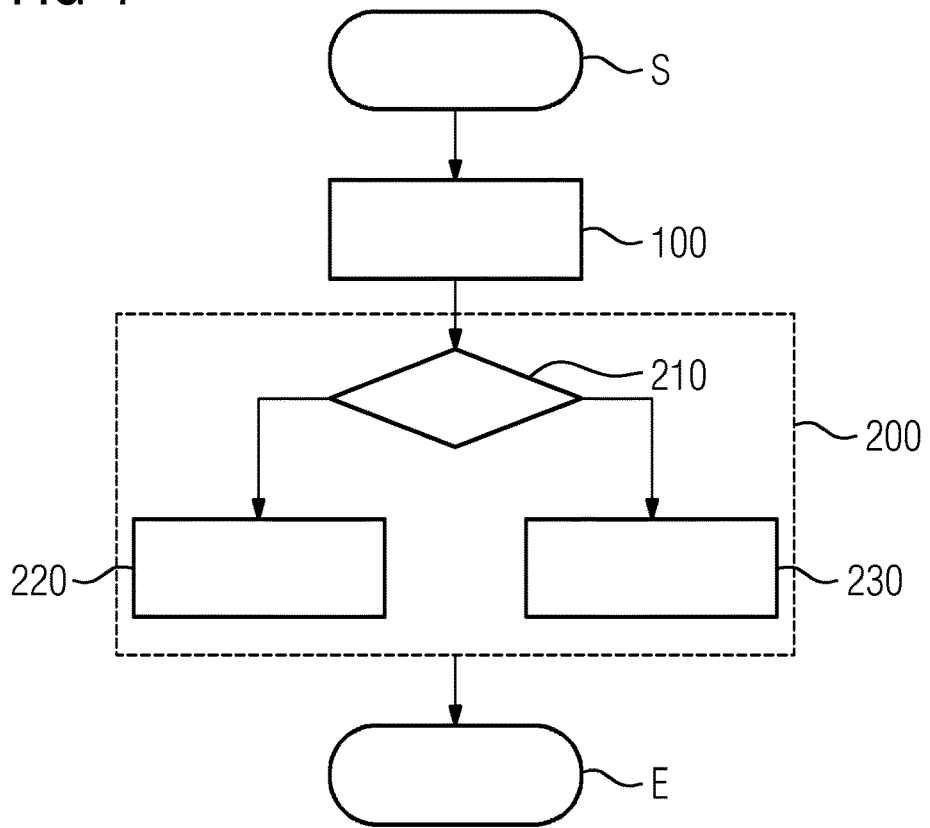
FIG. 4 a flowchart of a first embodiment of a combined method.

FIG. 4 is a flowchart of a first embodiment of a combined method. The combined method is a combination of the first method according to the invention for determining a similarity parameter for an original protocol with a reference protocol with a second method according to the invention for updating an original protocol. It differs from the embodiment shown in FIG. 2 in further method steps that follow method step 100 and which can be combined to form method step 200, the updating of the original protocol. According to an updating strategy, a selection 210 is made as to how the original protocol should be updated. Herein, with the selection 210, depending upon the similarity parameter determined in method step 100, in method step 220, the original protocol is retained or, in method step 230, the original protocol is replaced by a reference protocol. Steps 210, 220 and 230 can be combined in method step 200, the updating of the original protocol. Method step 100 is preferably performed by the determining processor 33 of the medical imaging apparatus. The method steps 200, 220, 230 and the selection 210 are preferably performed by the updating processor 34 of the medical imaging apparatus.

Figure 5:
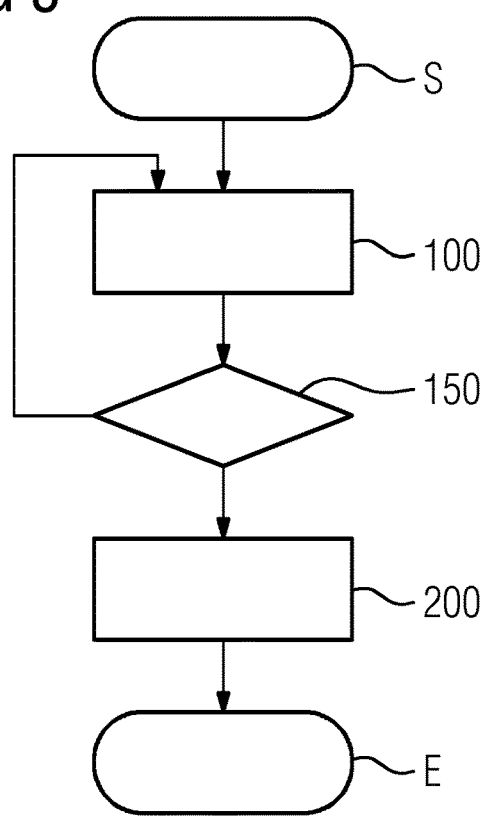
FIG. 5 is a flowchart of a second embodiment of a combined method.

FIG. 5 is a flowchart of a second embodiment of a combined method. Herein, a reference set comprising at least two reference protocols is provided. First, in method step 100 a similarity parameter is determined for the original protocol each with a first reference protocol comprised by the reference set. This is followed by a decision 150: if a further reference protocol comprised by the reference set is provided for which as yet no similarity parameter with the original protocol has been determined, method step 100 is performed for the further reference protocol. If a similarity parameter with the original protocol was determined for all reference protocols comprised by the reference set, the original protocol according to method step 200 is updated based on the determined similarity parameters and an updating strategy before the method is finished with E. The decision 150 can be reached by the determining processor 33 and/or by the updating processor 34 of the medical imaging apparatus.

The updating strategy is preferably designed such that the reference protocol for which the similarity parameter characterizes a smallest difference between the original protocol and the reference protocol replaces the original protocol during the updating in method step 200. The updating strategy can be determined by a user of the medical imaging apparatus 12.

Figure 6:
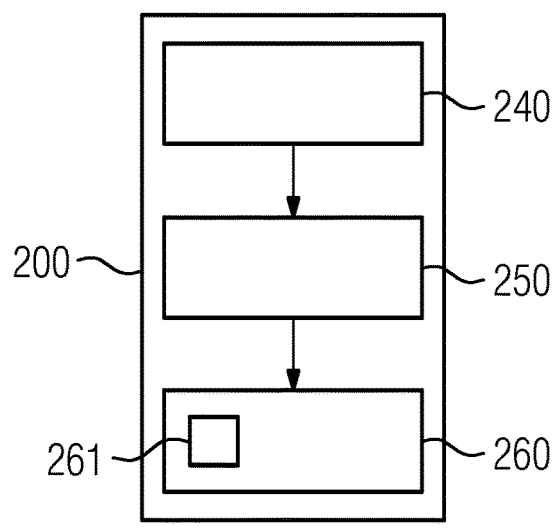
FIG. 6 is a portion of a flowchart of an embodiment of a second method according to the invention.

FIG. 6 shows portion of a flowchart of an embodiment of a second method according to the invention. This in particular shows an embodiment of method step 200, the updating of the original protocol, in more detail. First, in method step 240, the reference protocols comprised by the reference set can each be categorized in accordance with the respective similarity parameter into one of at least two categories. The reference protocols as a first one of the at least two categories can be provided in method step 250, wherein optionally a difference between at least one reference protocol comprised by the first category and the original protocol can be displayed. In method step 260, one of the reference protocols provided can be selected to replace the original protocol selected or the original protocol can be retained. For the selection to be made in method step 260, in a further method step 261 within method step 260, the medical imaging apparatus can be controlled according to the original protocol and/or according to at least one reference protocol. The method steps 200, 240, 250, 260 are preferably performed by means of the updating processor 34 of the medical imaging apparatus 12. The control of the medical imaging apparatus 12 is preferably initiated by the updating processor 34 and/or carried out by the control computer 24 of the medical imaging apparatus. The selection to be made in method step 260 can be made by a user via the input unit 26 and/or display unit 25 of the magnetic resonance apparatus 12.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for determining a similarity parameter for an original protocol for operating a medical imaging apparatus, with a reference protocol for operating the medical imaging apparatus, said method comprising:
providing a computer with an original protocol for operating a medical imaging apparatus, said original protocol comprising control parameters for controlling the medical imaging apparatus and being compatible with an original configuration of the medical imaging apparatus;
providing said computer with a reference protocol for operating the medical imaging apparatus, said reference protocol comprising control parameters for controlling the medical imaging apparatus and being compatible with a new configuration of the medical imaging apparatus, the new configuration corresponding to a change to one or more components of the medical imaging apparatus with respect to the original configuration; and
in said computer, executing a comparative analysis algorithm that produces a similarity parameter that is a measure of a similarity between the original protocol and the reference protocol.

2. A method as claimed in claim 1 further comprising, in said computer, converting the original protocol, based on the similarity parameter, to generate a converted original protocol that is compatible with the new configuration of the medical imaging apparatus.

3. A method as claimed in claim 2 wherein the original protocol is converted in the analysis algorithm to generate the converted original protocol.

4. A method as claimed in claim 1 comprising, in the execution of said comparative analysis, selecting corresponding control parameters respectively from said original protocol and said reference protocol and making a comparison between said corresponding parameters in order to produce said similarity parameter.

5. A method as claimed in claim 1 comprising receiving a manual entry into said computer that designates a set of control parameters in said original protocol, and executing said comparative algorithm to produce said similarity parameter dependent on said set of control parameters.

6. A method as claimed in claim 1 comprising:
in said computer, executing an updating strategy algorithm to which said similarity parameter is provided as an input, in order to produce an output of said updating strategy algorithm that designates whether said original protocol is retained or whether said original protocol is replaced by the reference protocol.

7. A method as claimed in claim 6 comprising:
providing said reference protocol to said computer in a reference protocol set that comprises at least two reference protocols;
for each reference protocol in said reference protocol set, determining said similarity parameter with said original protocol, thereby producing a plurality of similarity parameters; and
providing said plurality of similarity parameters as said input to said updating strategy algorithm, and executing said updating strategy algorithm to produce said output dependent on said plurality of similarity parameters.

8. A method as claimed in claim 7 comprising executing said updating strategy algorithm to identify a reference protocol in said reference protocol set for which said similarity parameter represents a smallest difference between said original protocol and the identified protocol, and wherein said output of said updating strategy algorithm is a replacement of said original protocol with said identified reference protocol.

9. A method as claimed in claim 7 comprising, in the execution of said updating strategy algorithm:
specifying at least two categories for the respective reference protocols in said reference protocol set;
using the respective similarity parameter for each reference protocol in said reference protocol set to place the respective reference protocols in a category among said at least two categories;
at a display monitor in communication with said computer, displaying the respective reference protocols in said reference protocol set organized to said categories in order to allow a user to select one of the displayed reference protocols; and
receiving a manual entry into said computer that designates said selection and, in said computer, selecting the reference protocol designated by said selection as the output of said updating strategy algorithm.

10. A method as claimed in claim 9 comprising, in said display of said reference protocols, displaying a difference between at least one reference protocol in at least one category, and said original protocol.

11. A method as claimed in claim 7 comprising, from said computer, controlling said medical imaging apparatus according to the output of said updating strategy algorithm.

12. A method as claimed in claim 6 comprising receiving a manual entry into said computer that determines said updating strategy algorithm.

13. A method as claimed in claim 6 comprising executing said updating strategy algorithm only when said new configuration is made available for operating said medical imaging apparatus.

14. A method as claimed in claim 1 further comprising: in said computer, generating an electrical signal that represents the similarity parameter and making the electrical signal available as an output from the computer.

15. A method as claimed in claim 1 wherein the one or more components include one or more hardware components of the medical imaging apparatus.

16. A method as claimed in claim 1 wherein the new configuration further corresponds to a change to software of the medical imaging apparatus with respect to the original configuration.

17. A method as claimed in claim 1 wherein the original and the new configurations are independent of an object to be examined.

18. A method as claimed in claim 1 wherein the original and the new configurations are independent of image data of an examination object.

19. A medical imaging apparatus comprising:
    a medical image data acquisition device; and
    a computer provided with an original protocol for operating the medical image data acquisition device, said original protocol comprising control parameters for controlling the medical image data acquisition device and being compatible with an original configuration of the medical image data acquisition device, and with a reference protocol for operating the medical image data acquisition device, said reference protocol comprising control parameters for controlling the medical image data acquisition device and being compatible with a new configuration of the medical image data acquisition device, the new configuration corresponding to a change to one or more components of the medical imaging apparatus with respect to the original configuration, wherein the computer is configured to execute a comparative analysis algorithm that produces a similarity parameter that is a measure of a similarity between the original protocol and the reference protocol.

20. A medical imaging apparatus as claimed in claim 19 wherein: said computer is configured to execute an updating strategy algorithm to which said similarity parameter is provided as an input, in order to produce an output of said updating strategy algorithm that designates whether said original protocol is retained or whether said original protocol is replaced by the reference protocol.

21. A non-transitory, computer-readable data storage medium encoded with programming instructions, said storage medium being loaded into a computer system of a medical imaging apparatus and said programming instructions causing said computer system to:
    receive an original protocol for operating a medical imaging apparatus, said original protocol comprising control parameters for controlling the medical imaging apparatus and being compatible with an original configuration of the medical imaging apparatus;
    receive a reference protocol for operating the medical imaging apparatus, said reference protocol comprising control parameters for controlling the medical imaging apparatus and being compatible with a new configuration of the medical imaging apparatus, the new configuration corresponding to a change to one or more components of the medical imaging apparatus with respect to the original configuration; and
    execute a comparative analysis algorithm that produces a similarity parameter that is a measure of a similarity between the original protocol and the reference protocol.

22. A storage medium as claimed in claim 21 wherein said programming instructions cause said computer system to:
    execute an updating strategy algorithm to which said similarity parameter is provided as an input, in order to produce an output of said updating strategy algorithm that designates whether said original protocol is retained or whether said original protocol is replaced by the reference protocol.

\* \* \* \* \*